(12) United States Patent
Scheuerman et al.

(10) Patent No.: US 7,767,649 B2
(45) Date of Patent: *Aug. 3, 2010

(54) AMINO ACID CONJUGATES PROVIDING FOR SUSTAINED SYSTEMIC CONCENTRATIONS OF GABA ANALOGUES

(75) Inventors: Randall A. Scheuerman, Santa Clara, CA (US); Mark A. Gallop, Los Altos, CA (US); Kenneth C. Cundy, Redwood City, CA (US); Ronald W. Barrett, Saratoga, CA (US)

(73) Assignee: XenoPort, Inc., Santa Clara, CA (US)

( * ) Notice: Subject to any disclaimer, the term of this patent is extended or adjusted under 35 U.S.C. 154(b) by 349 days.

This patent is subject to a terminal disclaimer.

(21) Appl. No.: 11/654,598

(22) Filed: Jan. 18, 2007

(65) Prior Publication Data

US 2007/0135356 A1 Jun. 14, 2007

Related U.S. Application Data

(62) Division of application No. 10/436,100, filed on May 13, 2003, now Pat. No. 7,183,259.

(60) Provisional application No. 60/381,604, filed on May 17, 2002.

(51) Int. Cl.
*A61K 38/04* (2006.01)
(52) U.S. Cl. .......................................... 514/19; 530/331
(58) Field of Classification Search .................. None
See application file for complete search history.

(56) References Cited

U.S. PATENT DOCUMENTS

| 3,845,770 A | 11/1974 | Theeuwes et al. |
| 3,916,899 A | 11/1975 | Theeuwes et al. |
| 4,024,175 A | 5/1977 | Satzinger et al. |
| 4,087,544 A | 5/1978 | Satzinger et al. |
| 5,084,479 A | 1/1992 | Woodruff |
| 5,563,175 A | 10/1996 | Silverman et al. |
| 6,001,876 A | 12/1999 | Singh |
| 6,020,370 A | 2/2000 | Horwell et al. |
| 6,028,214 A | 2/2000 | Silverman et al. |
| 6,103,932 A | 8/2000 | Horwell et al. |
| 6,117,906 A | 9/2000 | Silverman et al. |
| 7,183,259 B2 * | 2/2007 | Scheuerman et al. .......... 514/18 |

FOREIGN PATENT DOCUMENTS

| WO | WO 92/09560 | 6/1992 |
| WO | WO 93/23383 | 11/1993 |
| WO | WO 99/31057 | 6/1994 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08671 | 2/1999 |
| WO | WO 99/21824 | 5/1999 |
| WO | WO 99/31075 | 6/1999 |
| WO | WO 99/37296 | 7/1999 |
| WO | WO 99/61424 | 12/1999 |
| WO | WO 00/23067 | 4/2000 |
| WO | WO 00/31020 | 6/2000 |
| WO | WO 00/50027 | 8/2000 |
| WO | WO 01/20331 | 3/2001 |
| WO | WO 02/00209 | 1/2002 |
| WO | WO 02/28411 A1 | 4/2002 |
| WO | WO 02/32376 A2 | 4/2002 |
| WO | WO 02/100344 A2 | 12/2002 |

OTHER PUBLICATIONS

A. Tsuji et al., "Carrier-Mediated Intestinal Transport of Drugs," *Pharmaceutical Research*, vol. 13, No. 7, 1996, pp. 963-977.
F.H. Leibach et al., "Peptide transporters in the Intestine and the Kidney," *Annu. Rev. Nutr.*, vol. 16, 1996, pp. 99-119.
M.A. Navia et al., "Design principles for orally bioavailable drugs," *DDT*, vol. 1, No. 5, 1996, pp. 179-189.
H. Wang et al., "Electrophysiological characteristics of the proton-coupled peptide transporter PEPT2 cloned from rat brain," *Am. Physiological Society*, 1998, pp. C967-C975.
S. A. Adibi, "The oligopeptide transporter (Pept-1) in Human Intestine: Biology and Function," *Gastroenterology*, vol. 113, 1997, pp. 332-340.
S.T. Dieck et al., "The peptide transporter PepT2 is expressed in Rat Brain and Mediates the Accumulation of the . . . ", *GLIA*, vol. 25, 1999, pp. 10-20.
R.K. Verma et al., "Osmotically Controlled Oral Drug Delivery," *Drug Development and Industrial Pharmacy*, vol. 26, No. 7, 2000, pp. 695-708.
Fosker & Law, "L-Glutamyl-Gamma-Aminobutyric Acid and Related Compounds", *J. Chem. Soc.*, 1965, pp. 7305-5312.
Nielsen et al., "Model prodrugs for the intestinal oligopeptide transporter model drug release in aqueous solution and in various biological media", *Journal of Controlled Release*, May 18, 2001, vol. 73, No. 1, pp. 21-30.
Lee et al., "Pharmacogenomics of drug transporters: the next drug delivery challenge", *Advanced Drug Delivery Reviews*, Oct. 1, 2001, vol. 50, No. Suppl. 1.
EPO Annex to Form PCT/ISA/206 Communication Relating to the Results of the Partial International Search mailed Nov. 14, 2003.

* cited by examiner

*Primary Examiner*—Christopher R. Tate
*Assistant Examiner*—Roy Teller
(74) *Attorney, Agent, or Firm*—D. Byron Miller; Lucy S. Chang

(57) ABSTRACT

This invention is directed to compounds that provide for sustained systemic concentrations of GABA analogs following administration to animals. This invention is also directed to pharmaceutical compositions including and methods using such compounds.

4 Claims, 10 Drawing Sheets

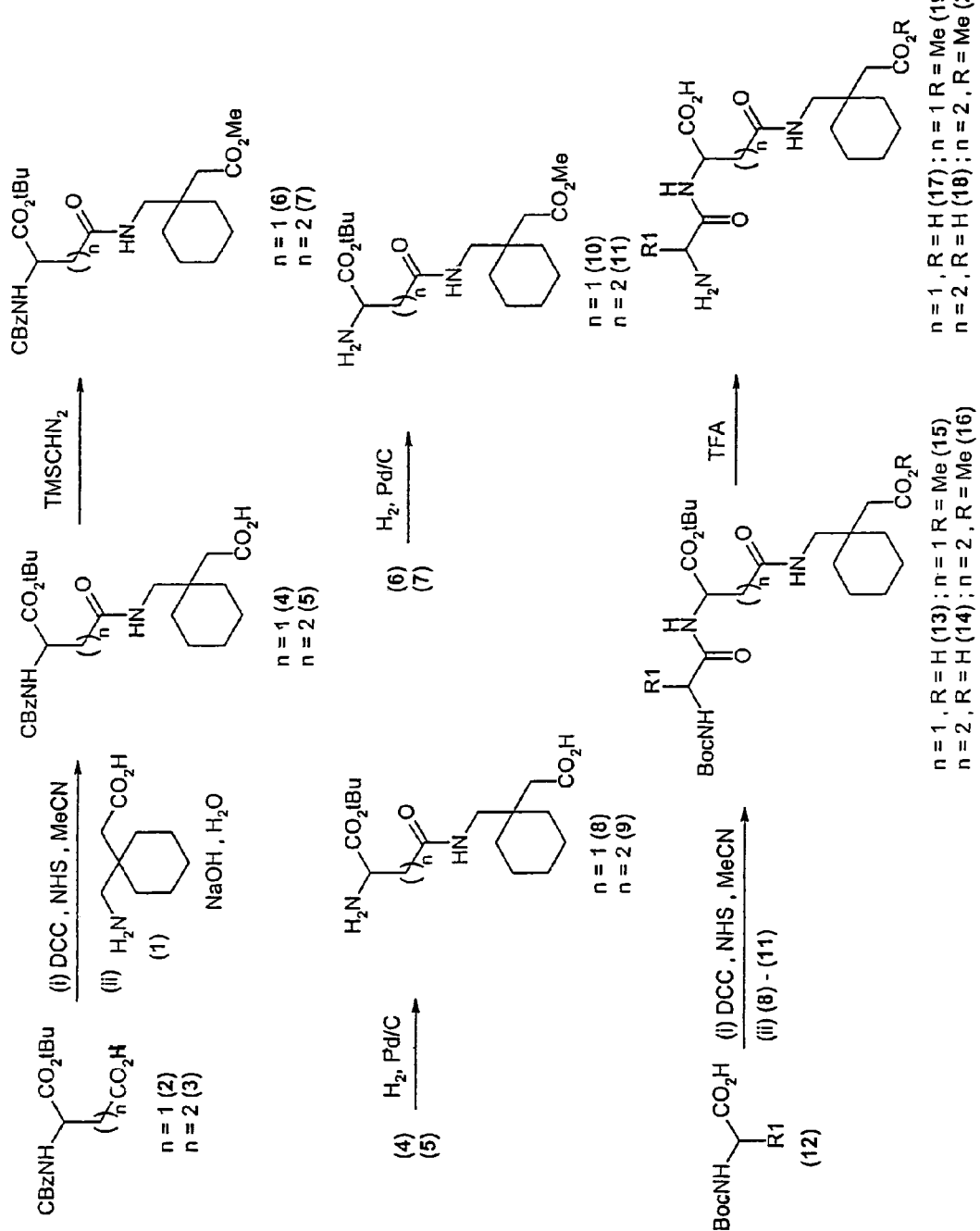
Figure 1: GABA Analogs Conjugated via Amide Linkages -1

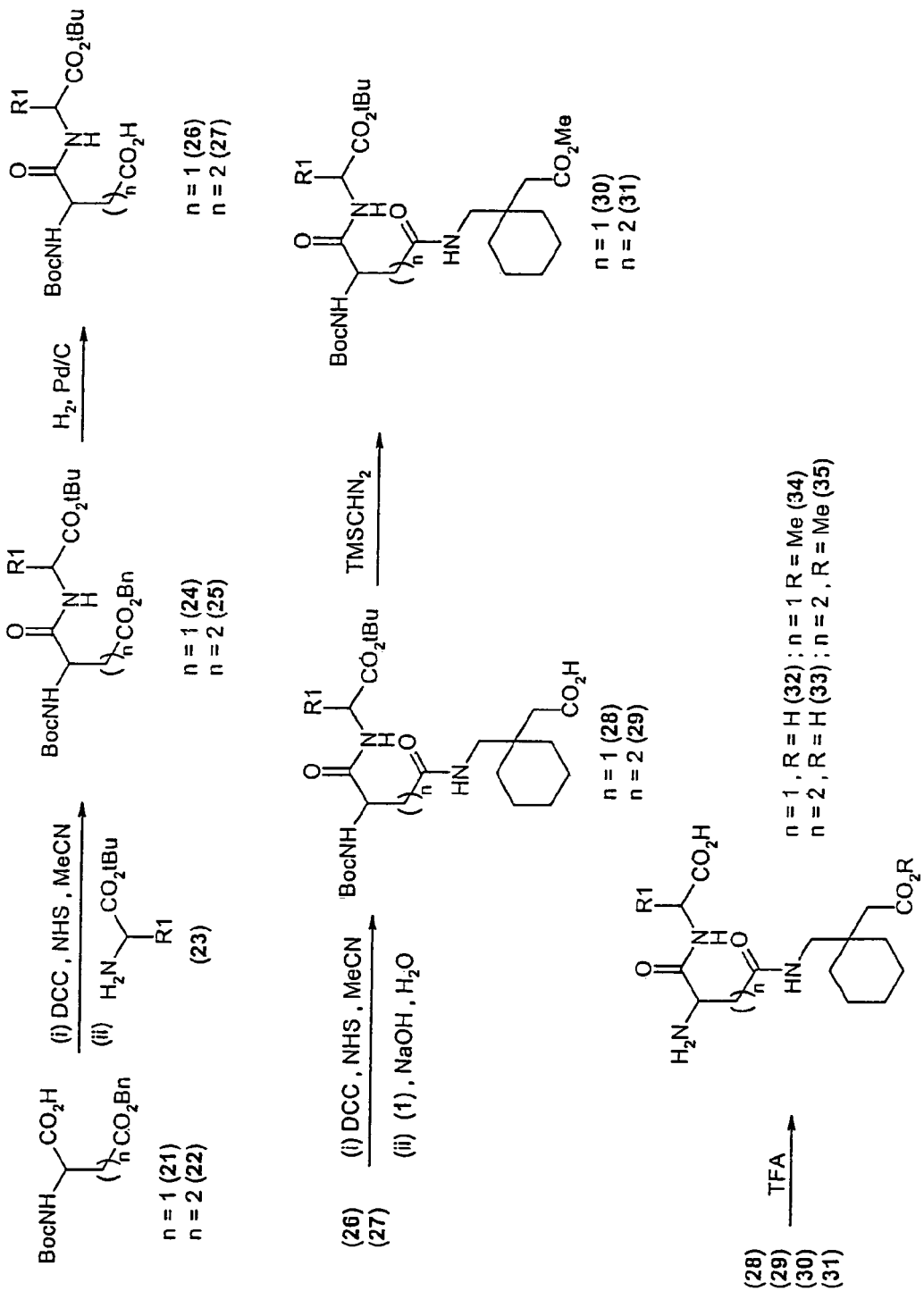
Figure 2: GABA Analogs Conjugated via Amide Linkages - 2

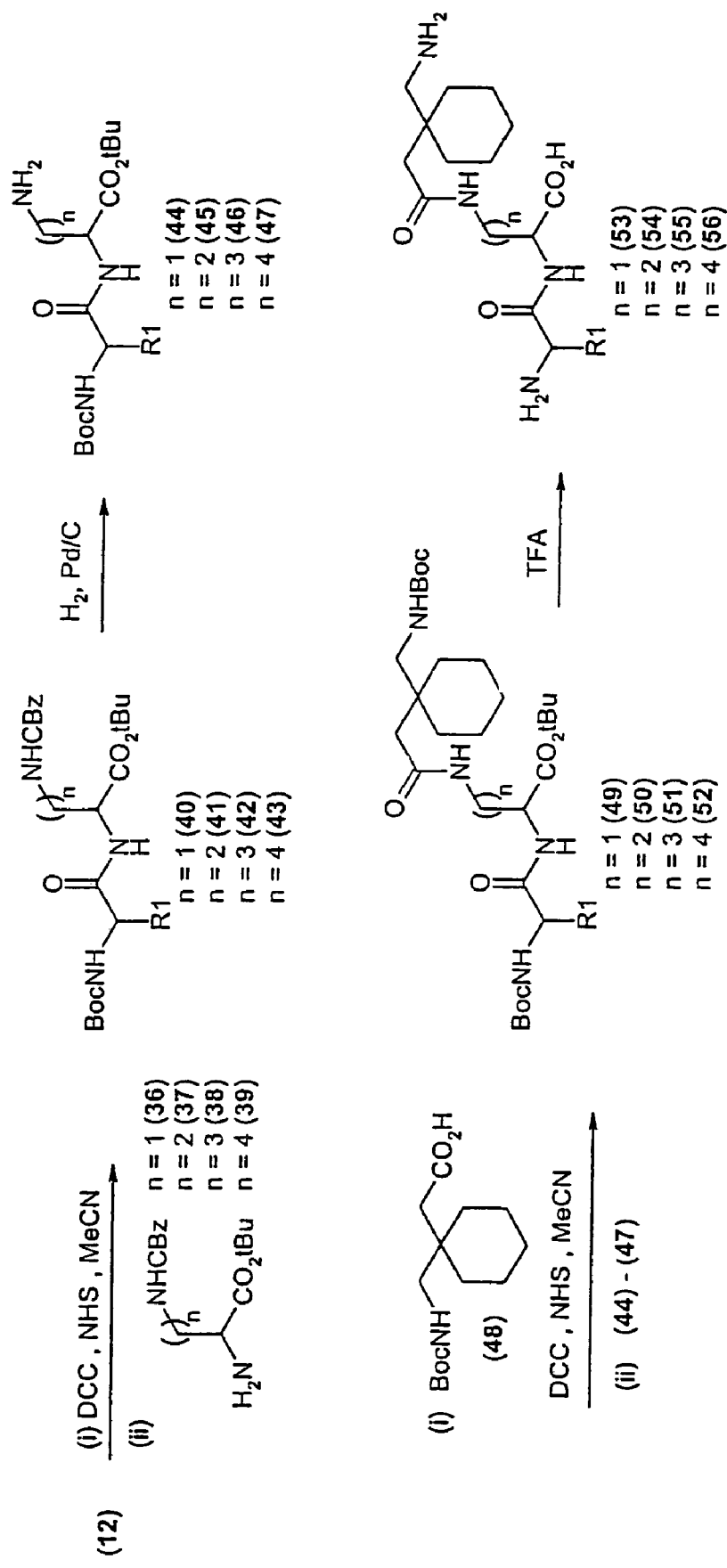
Figure 3: GABA Analogs Conjugated via Amide Linkages - 3

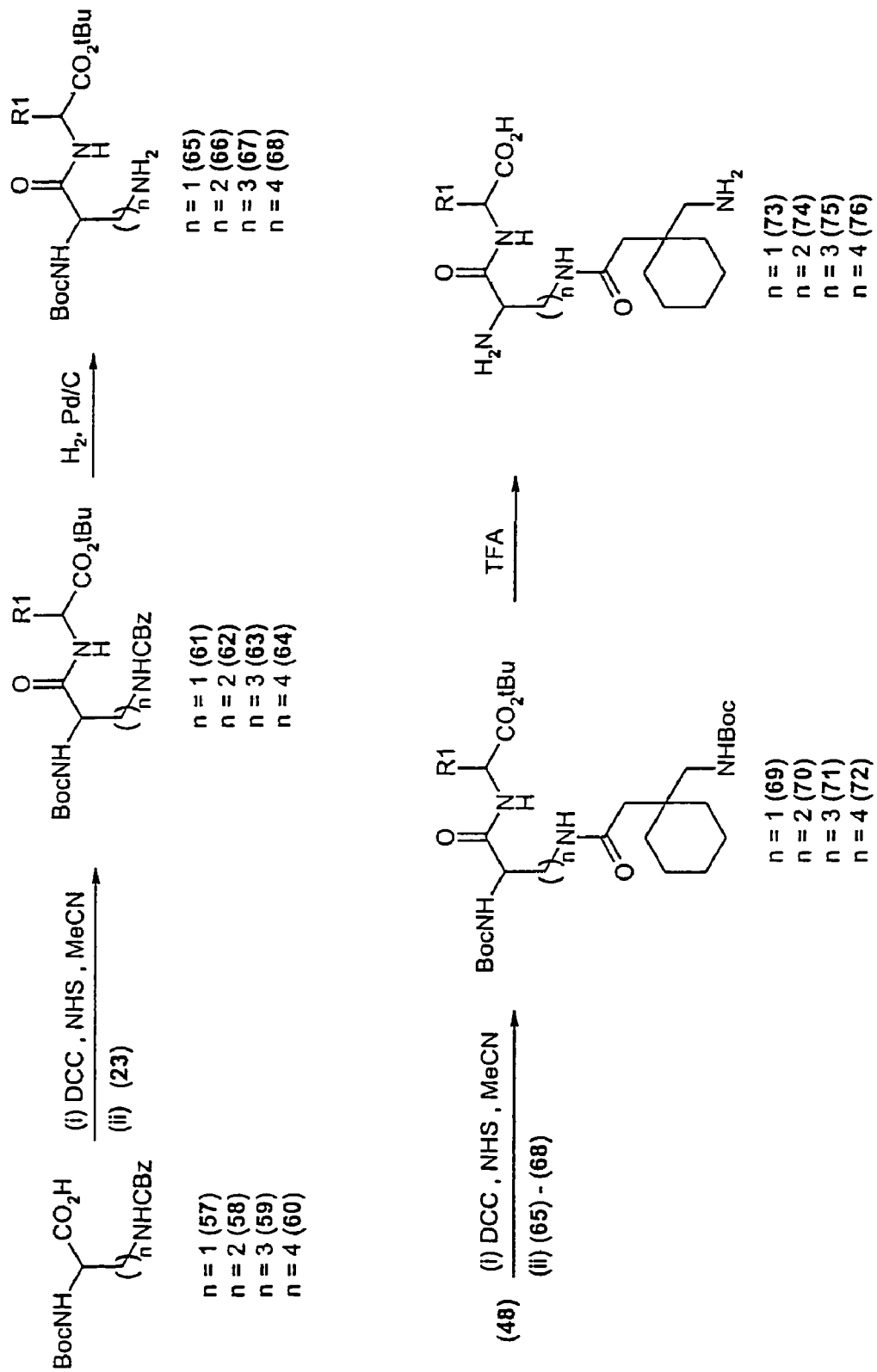
Figure 4: GABA Analogs Conjugated via Amide Linkages - 4

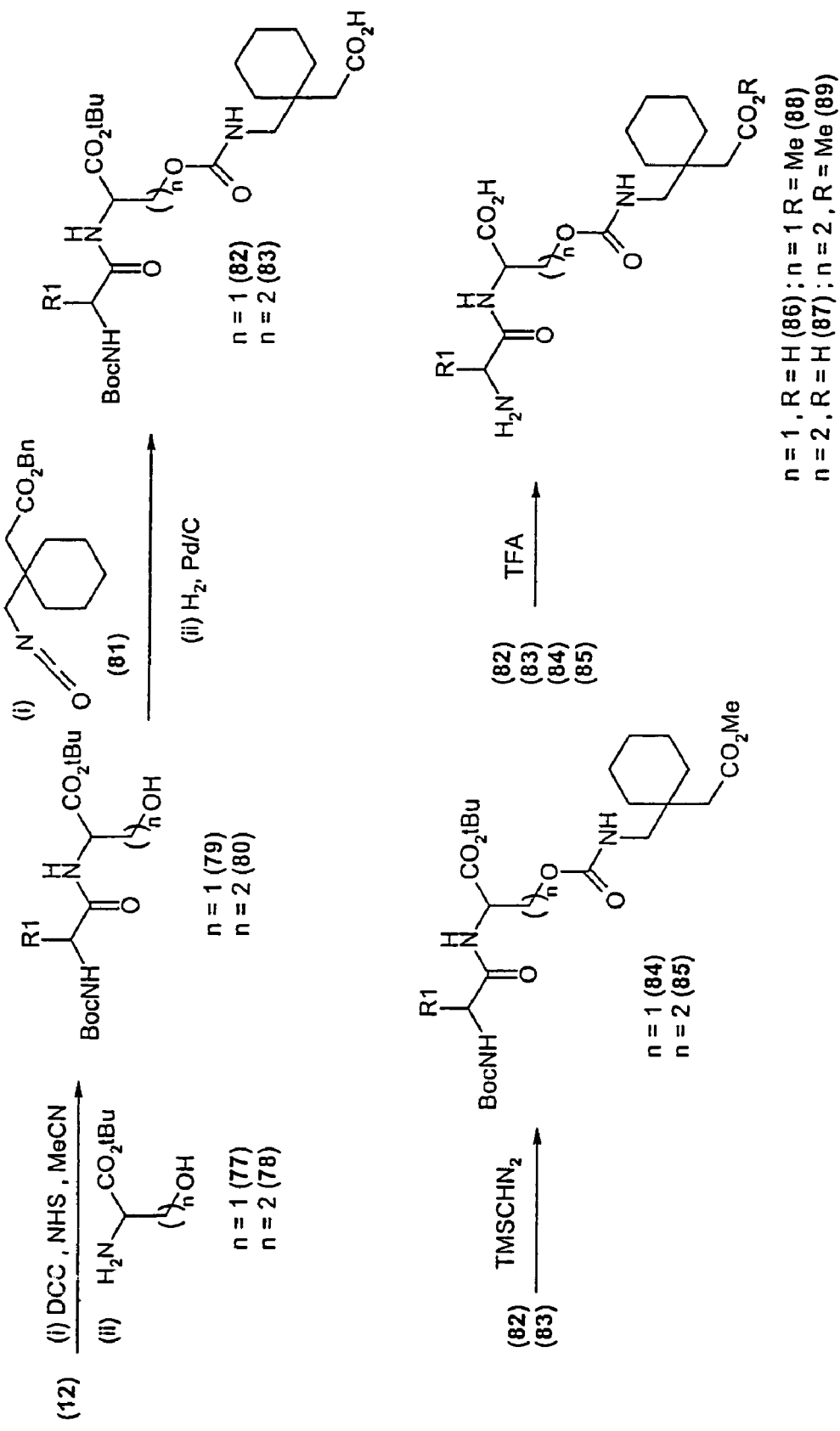
Figure 5: GABA Analogs Conjugated via Carbamate Linkages -1

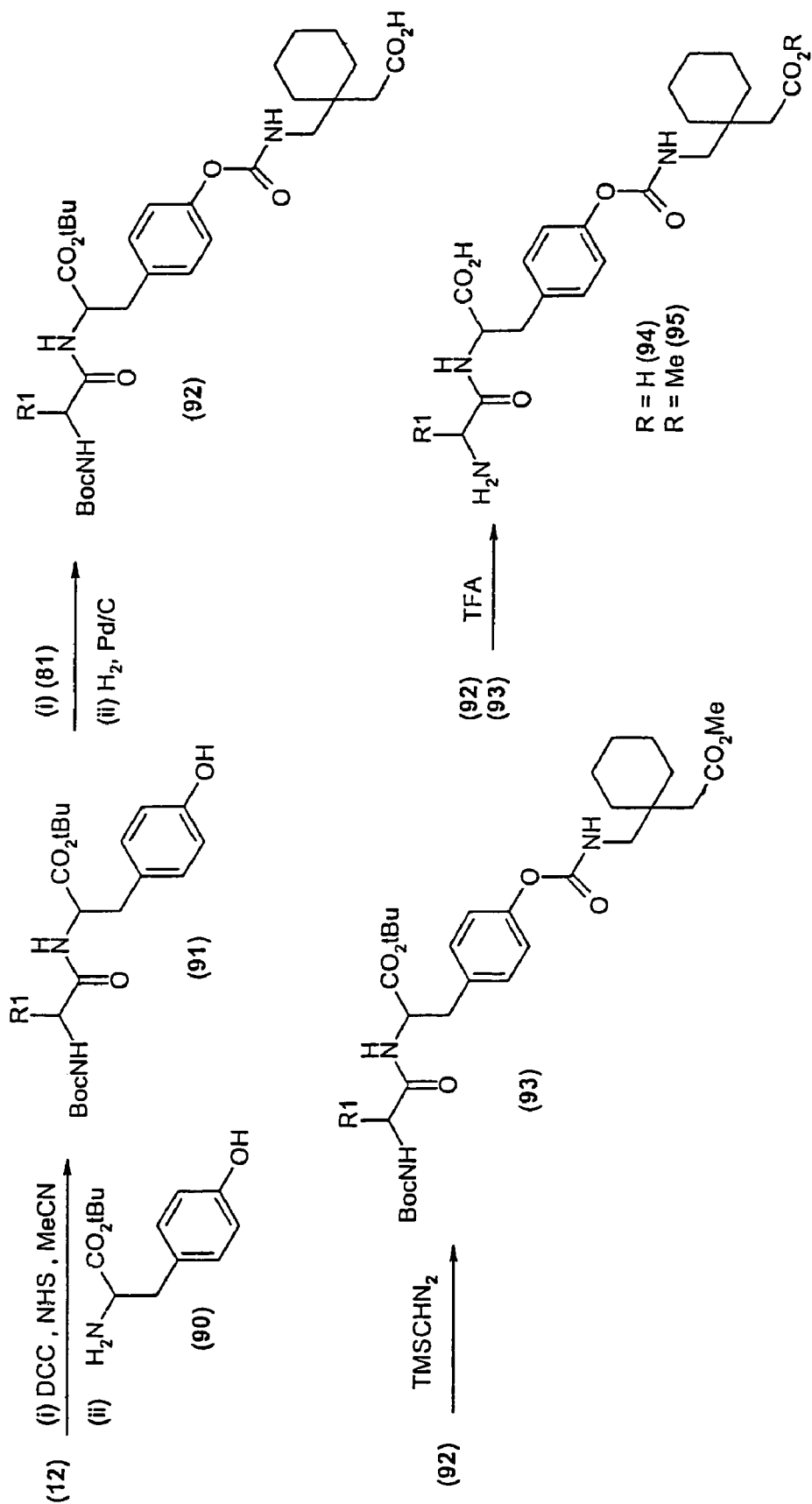
Figure 6: GABA Analogs Conjugated via Carbamate Linkages - 2

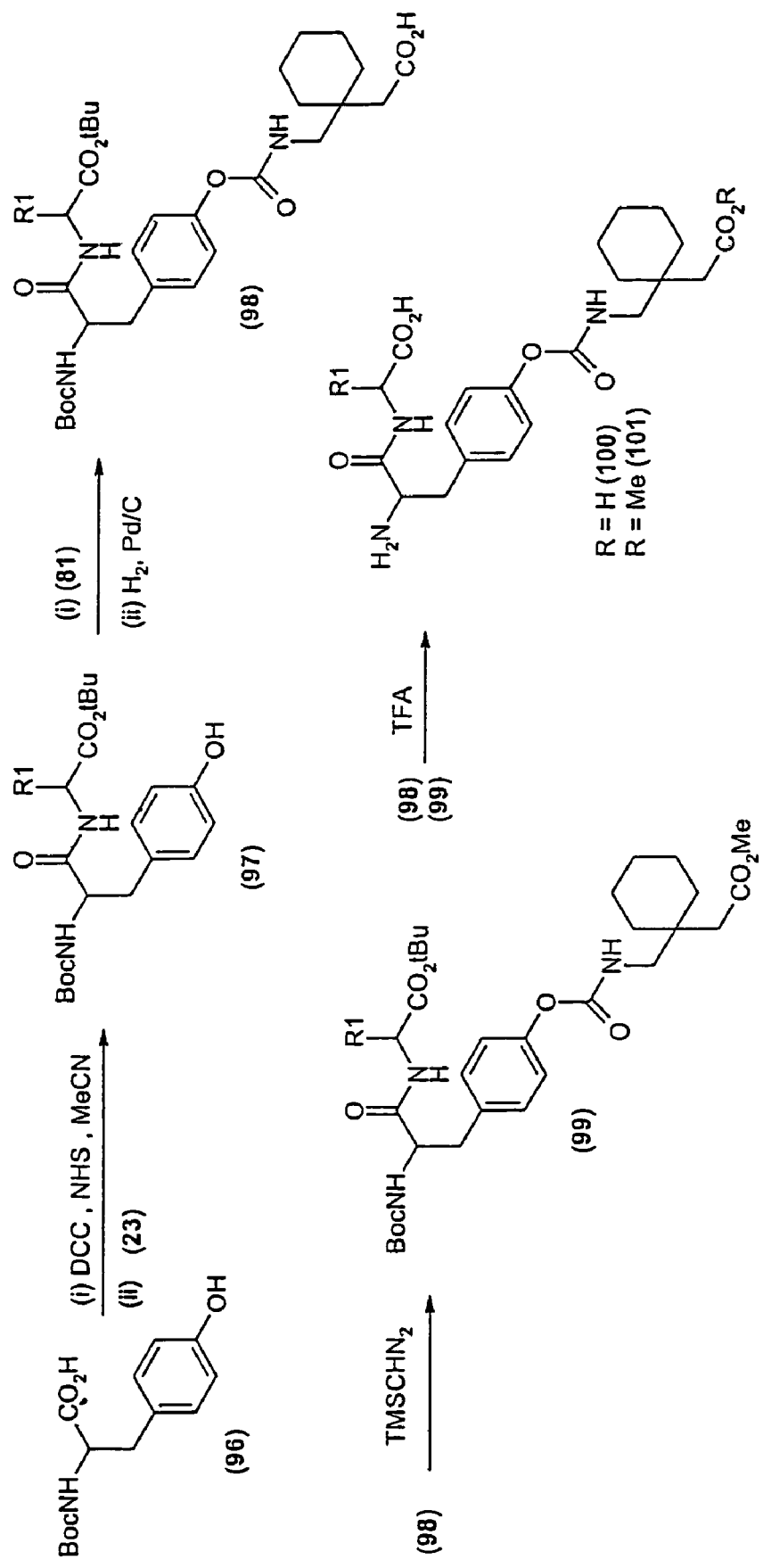
Figure 7: GABA Analogs Conjugated via Carbamate Linkages - 3

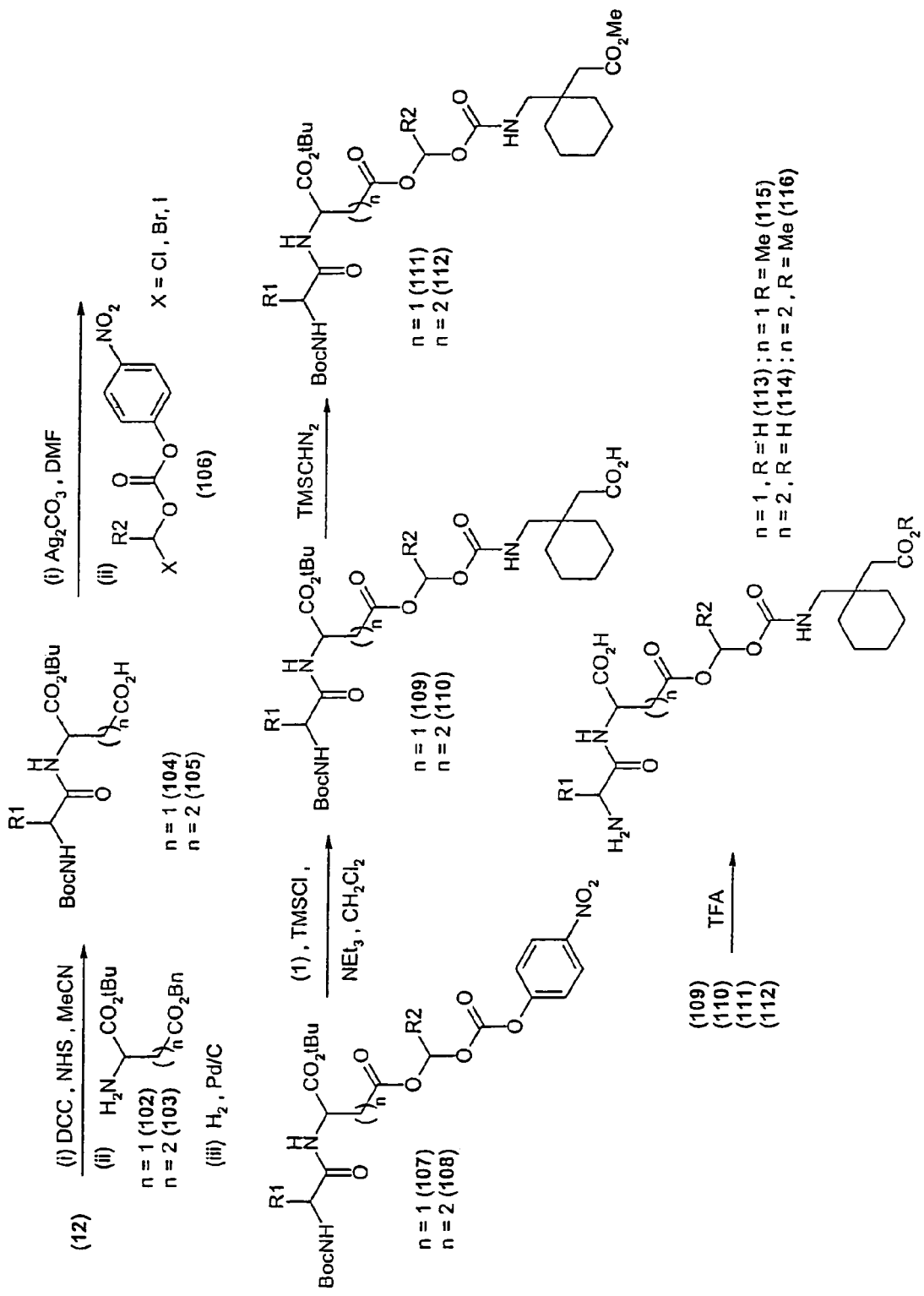
Figure 8: GABA Analogs Conjugated via Acyloxyalkylcarbamate Linkages - 1

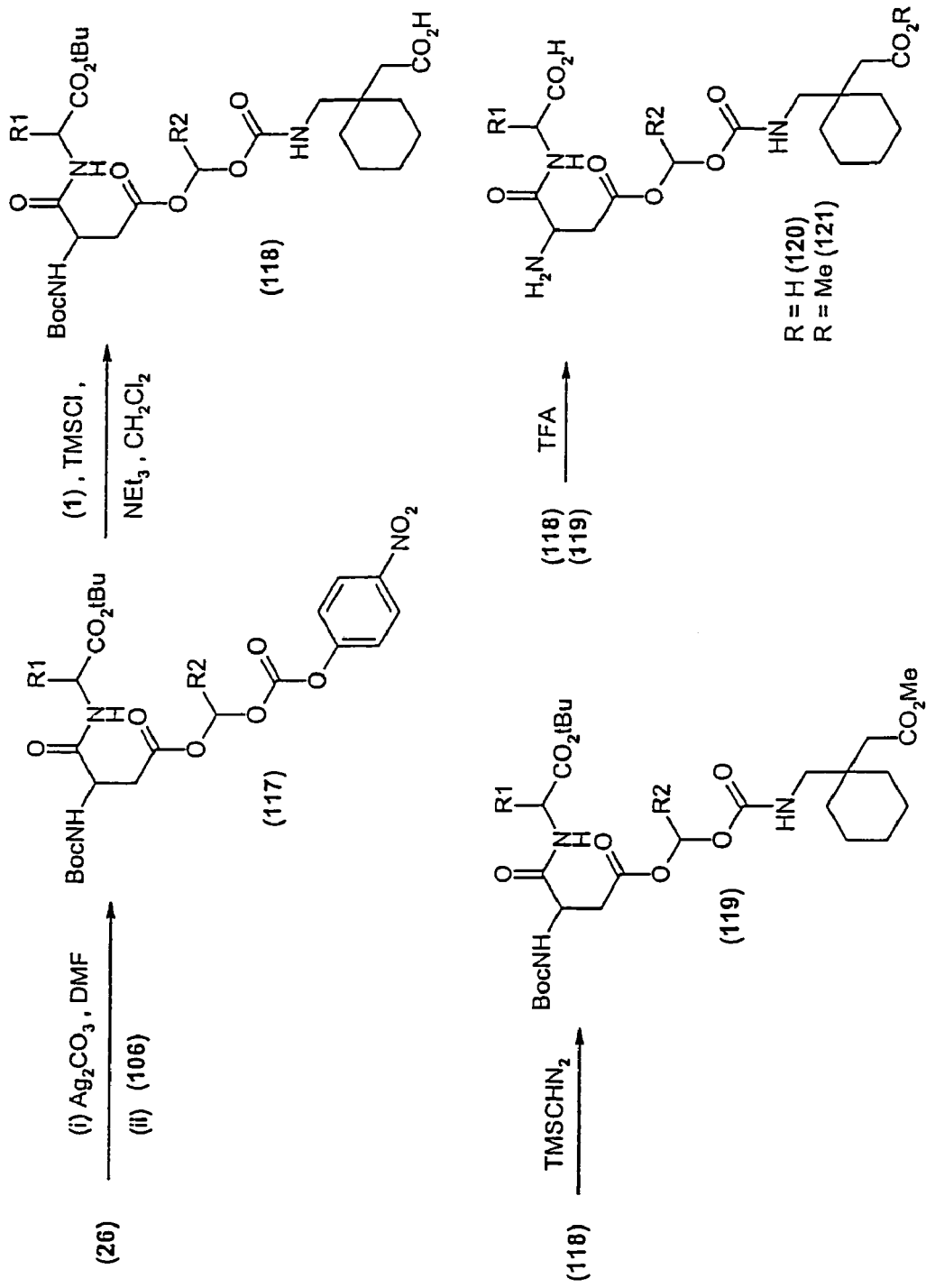
Figure 9: GABA Analogs Conjugated via Acyloxyalkylcarbamate Linkages - 2

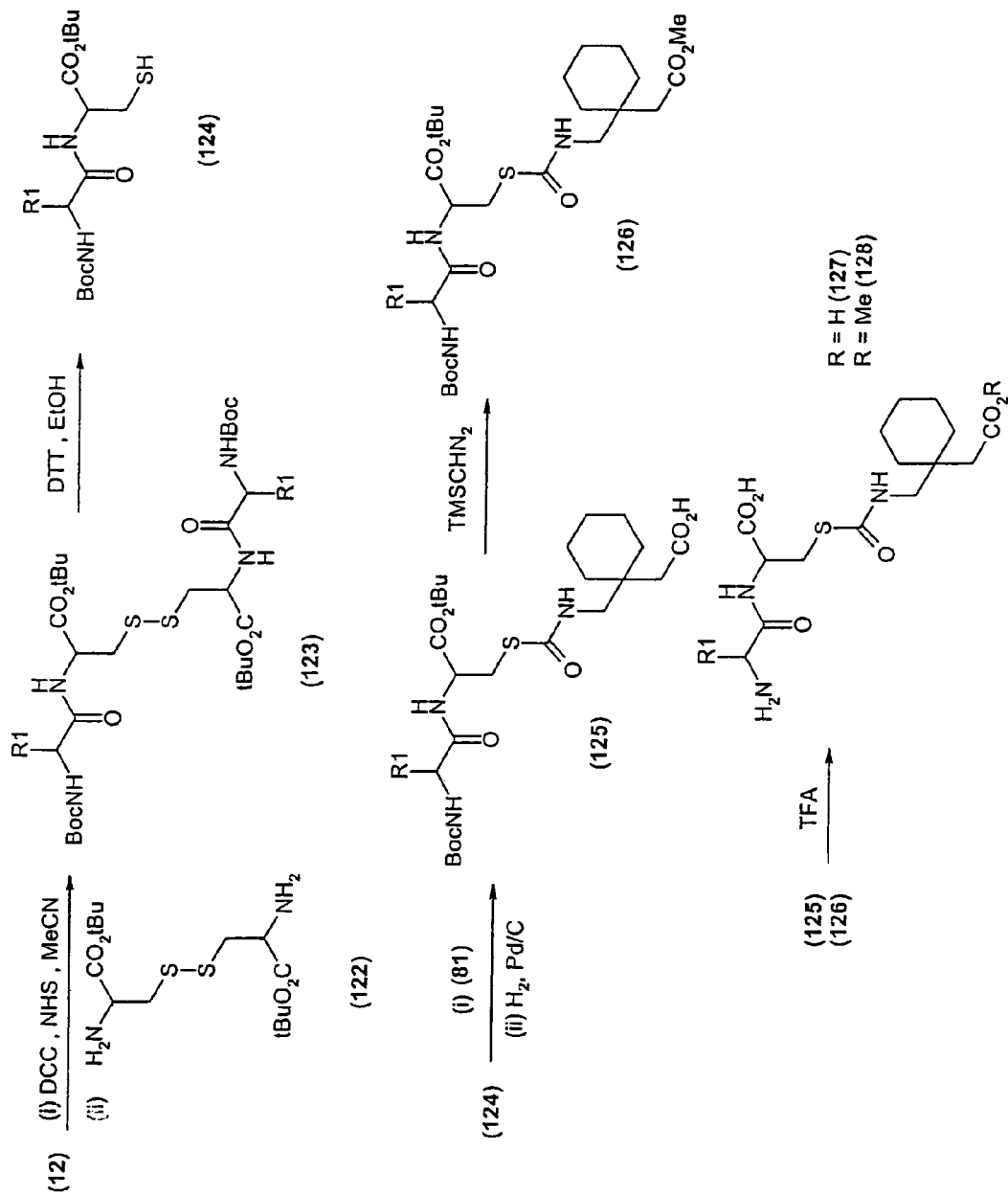
Figure 10: GABA Analogs Conjugated via Thiocarbamate Linkage

AMINO ACID CONJUGATES PROVIDING FOR SUSTAINED SYSTEMIC CONCENTRATIONS OF GABA ANALOGUES

CROSS-REFERENCE TO RELATED APPLICATIONS

This application is a divisional of U.S. patent application Ser. No. 10/436,100 filed on May 13, 2003, issued as U.S. Pat. No. 7,183,259, which claims the benefit of U.S. Provisional Patent Application No. 60/381,604 filed on May 17, 2002, the disclosures of which are incorporated by reference in their entirety.

BACKGROUND OF THE INVENTION

1. Field of the Invention

This invention is directed to compounds that provide for sustained systemic concentrations of GABA analogs following administration to animals. This invention is also directed to pharmaceutical compositions and methods of use that employ such compounds.

2. State of the Art

Rapid clearance of drugs from the systemic circulation represents a major impediment to effective clinical use of therapeutic and/or prophylactic compounds. Although multiple factors can influence the systemic concentrations of drugs achieved following administration (including drug solubility, dissolution rate, first-pass metabolism, p-glycoprotein and related efflux mechanisms, hepatic/renal elimination, etc), rapid systemic clearance is a particularly significant reason for suboptimal systemic exposure to many compounds. Rapid systemic clearance may require that large doses of drug be administered to achieve a therapeutic or prophylactic effect. Such larger doses of the drug, however, may result in greater variability in drug exposure, more frequent occurrence of side effects, or decrease in patient compliance. Frequent drug administration may also be required to maintain systemic drug levels above a minimum effective concentration. This problem is particularly significant for drugs that must be maintained in a well-defined concentration window to provide continuous therapeutic or prophylactic benefit while minimizing adverse effects (including for example, antibacterial agents, antiviral agents, anticancer agents, anticonvulsants, anticoagulants, etc.).

Conventional approaches to extend the systemic exposure of drugs with rapid clearance involve the use of formulation or device approaches that provide a slow or sustained release of drug within the intestinal lumen. These approaches are well known in the art and normally require that the drug be well absorbed from the large intestine, where such formulations are most likely to reside while releasing the drug. Drugs that are amenable to conventional sustained release approaches must be orally absorbed in the intestine and traverse this epithelial barrier by passive diffusion across the apical and basolateral membranes of the intestinal epithelial cells. The physicochemical features of a molecule that favor its passive uptake from the intestinal lumen into the systemic circulation include low molecular weight (e.g. <500 Da), adequate solubility, and a balance of hydrophobic and hydrophilic character (log P generally 1.5-4.0) (Navia and Chaturvedi, P. R. *Drug Discovery Today* 1996, 1, 179-189).

Polar or hydrophilic compounds are typically poorly absorbed through an animal's intestine, as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes, which result in movement of the substrate(s) across the membrane.

Over the past 10-15 years, it has been found that a number of orally administered drugs are recognized as substrates by some of these transporter proteins, and that this active transport may largely account for the oral absorption of these molecules (Tsuji and Tamai, *Pharm. Res.* 1996, 13, 963-977). While in most instances the transporter substrate properties of these drugs were unanticipated discoveries made through retrospective analysis, it has been appreciated that, in principle, one might achieve good intestinal permeability for a drug by designing in recognition and uptake by a nutrient transport system. Drugs subject to active absorption in the small intestine are often unable to passively diffuse across epithelial cell membranes and are too large to pass through the tight junctions that exist between the intestinal cells. These drugs include many compounds structurally related to amino acids, dipeptides, sugars, nucleosides, etc. (for example, many cephalosporins, ACE inhibitors, AZT, gabapentin, pregabalin, baclofen, etc.)

One pathway that might provide for the sustained delivery of drugs with rapid systemic clearance is the proton-coupled peptide transporters (Leibach and Ganapathy, *Ann. Rev. Nutr.* 1996, 16, 99-119). Such transporters mediate the cellular uptake of small intact peptides consisting of two or three amino acids and are found primarily in the intestine and kidney. In the intestine, where small peptides are not well-absorbed through passive diffusion, the transporters act as a vehicle for their effective absorption. Transporters in the kidney actively reabsorb di- and tri-peptides from the glomerular filtrate, thereby increasing their half-life in the circulation.

Two proton-coupled peptide transporters that have been cloned and characterized are PEPT1 and PEPT2. PEPT1 is a low-affinity, high-capacity transporter found primarily in the intestine. The human PEPT1 consists of 708 amino acids and possesses 12 putative transmembrane domains. PEPT2, in contrast, is a high-affinity, low-capacity transporter found mostly in the kidney. It consists of 729 amino acids and is 50% identical to human intestinal PEPT1.

Studies of PEPT1 and PEPT2 have shown that the transporters account for the absorption and reabsorption of certain therapeutically active compounds. The compounds include both biologically active peptides (e.g., renin inhibitors) and zwitterionic antibiotics. Based on these observations, researchers have suggested that peptide transporters, in conjunction with cytosolic peptidases, could be exploited for systemic delivery of certain drugs in the form of peptide prodrugs. Dipeptide analogues of α-methyldopa, L-α-methyldopa-Phe and L-α-methyldopa-Pro, for example, are absorbed more efficiently in the intestine than α-methyldopa alone. Once across the intestinal membrane, the dipeptides are hydrolyzed by cytosolic peptidases to release α-methyldopa.

While the general suggestion of exploiting proton-coupled peptide transporters to enhance the absorption of poorly absorbed drugs has been made, the existing art does not teach a method that can be used successfully to design and construct a peptide prodrug of any given drug. Moreover, while the existing art discusses improving intestinal absorption of poorly absorbed drugs, it does not teach methods for achieving sustained systemic concentrations of drugs following administration to animals.

SUMMARY OF THE INVENTION

This invention is directed to novel compounds that can be utilized to provide sustained systemic concentrations of drugs administered to an animal. This invention, therefore, permits sustained therapeutic or prophylactic systemic blood concentrations of GABA analogues that heretofore could not be achieved.

Accordingly, in one of its compound aspects, this invention is directed to a compound of Formula (I) or (II):

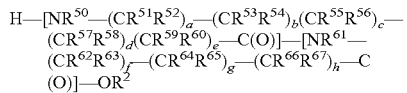

or

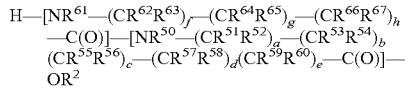

and pharmaceutically acceptable salts thereof;

wherein a, b, c, d, e, f, g and h are independently 0 or 1, provided that at least one of a, b, c, d, or e is 1; and further at least one of f, g and h is 1;

$R^2$ is hydrogen, alkyl, substituted alkyl, alkenyl, substituted alkenyl, alkynyl, aryl, substituted aryl, heteroaryl or substituted heteroaryl;

$R^{50}$ is hydrogen, alkyl, substituted alkyl, alkenyl, substituted alkenyl, alkynyl, aryl, substituted aryl, heteroaryl, substituted heteroaryl or $R^{50}$ and $R^{51}$ together with the atoms to which they are attached form a heterocyclyl ring;

$R^{51}$ is $R^{51'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring;

$R^{52}$ is $R^{52'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53}$ is $R^{53'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53}$ and $R^{54}$ together with the atoms to which they are attached form a cycloalkyl, substituted cycloalkyl, heterocyclyl or substituted heterocyclyl ring;

$R^{54}$ is $R^{54'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{55}$ is $R^{55'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{55}$ and $R^{56}$ together with the atoms to which they are attached form a cycloalkyl, substituted cycloalkyl, heterocyclyl or substituted heterocyclyl ring;

$R^{56}$ is $R^{56'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{57}$ is $R^{57'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{57}$ and $R^{58}$ together with the atoms to which they are attached form a cycloalkyl, substituted cycloalkyl, heterocyclyl or substituted heterocyclyl ring;

$R^{58}$ is $R^{58'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{59}$ is $R^{59'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{59}$ and $R^{60}$ together with the atoms to which they are attached form a cycloalkyl, substituted cycloalkyl, heterocyclyl or substituted heterocyclyl ring;

$R^{60}$ is $R^{60'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{61}$ is hydrogen, alkyl, substituted alkyl, alkenyl, substituted alkenyl, alkynyl, substituted alkynyl, aryl, substituted aryl, heteroaryl, substituted heteroaryl or $R^{61}$ and $R^{62}$ together with the atoms to which they are attached form a heterocyclyl ring;

$R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{62}$ and $R^{63}$ together with the atoms to which they are attached form a cycloalkyl, substituted cycloalkyl, heterocyclyl or substituted heterocyclyl ring;

$R^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{64}$ and $R^{65}$ together with the atoms to which they are attached form a cycloalkyl, substituted cycloalkyl, heterocyclyl or substituted heterocyclyl ring;

$R^{65}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{66}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{66}$ and $R^{67}$ together with the atoms to which they are attached form a cycloalkyl, substituted cycloalkyl, heterocyclyl or substituted heterocyclyl ring;

$R^{67}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

and wherein each of $R^{51'}$ through $R^{60'}$ is independently selected from the group consisting of alkylene-D, substituted alkylene-D, alkenylene-D, substituted alkenylene-D, alkynylene-D, substituted alkynylene-D, cycloalkylene-D, substituted cycloalkylene-D, heterocyclylene-D, substituted heterocyclylene-D, arylene-D, substituted arylene-D, heteroarylene-D and substituted heteroarylene-D, wherein D is selected from the group consisting of:

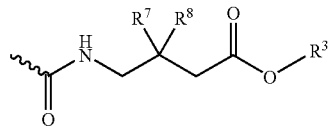

i

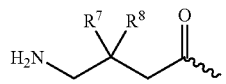

ii

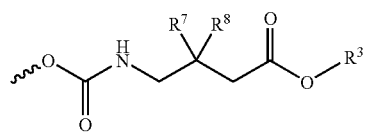

iii

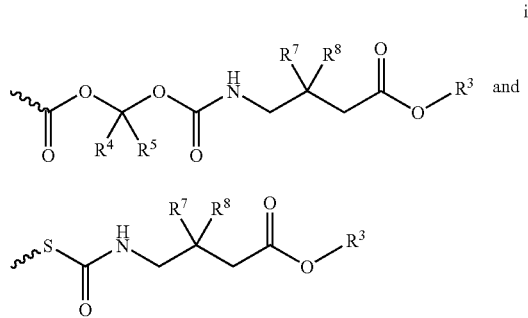

iv and v wherein $R^3$ is hydrogen, alkyl, substituted alkyl, alkenyl, substituted alkenyl, alkynyl, aryl, substituted aryl, heteroaryl and substituted heteroaryl;

each $R^4$ and $R^5$ are independently selected from the group consisting of hydrogen, alkyl, substituted alkyl, alkoxycarbonyl, substituted alkoxycarbonyl, aryl, substituted aryl, carbamoyl, cycloalkyl, substituted cycloalkyl, cycloalkoxycarbonyl, substituted cycloalkoxycarbonyl, heteroaryl, substituted heteroaryl, or optionally, $R^4$ and $R^5$ together with the carbon atom to which they are attached form a cycloalkyl, substituted cycloalkyl, heterocyclyl or substituted heterocyclyl ring;

each $R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;

provided that at least one of $R^{51}$ through $R^{60}$ is $R^{51'}$ through $R^{60'}$;

In a preferred embodiment, a, b, c, d, e, f, g and h are selected to provide a dipeptide composed of two α-amino acids, i.e., a=1; b, c, d and e=0; f=1, g and h=0. Particularly preferred compounds can be represented by Formulae (III) and (IV):

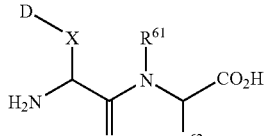

(III)

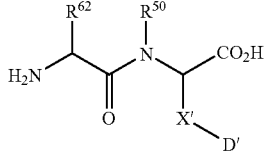

(IV)

and pharmaceutically acceptable salts thereof;

where X and X' are independently selected from the group consisting of alkylene, substituted alkylene, alkenylene, substituted alkenylene, alkynylene, substituted alkynylene, cycloalkylene, substituted cycloalkylene, heterocyclylene, substituted heterocyclylene, arylene, substituted arylene, heteroarylene and substituted heteroarylene;

D and D' are independently selected from the group consisting of:

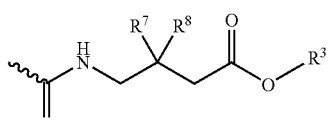

i

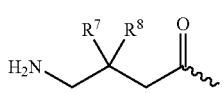

ii

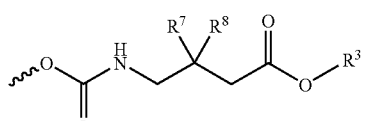

iii

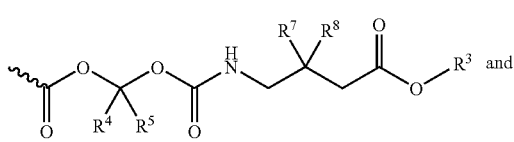

iv and v

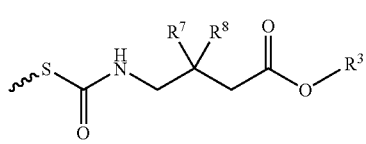

wherein $R^3$ is hydrogen, alkyl, substituted alkyl, alkenyl, substituted alkenyl, alkynyl, aryl, substituted aryl, heteroaryl and substituted heteroaryl;

each $R^4$ and $R^5$ are independently selected from the group consisting of hydrogen, alkyl, substituted alkyl, alkoxycarbonyl, substituted alkoxycarbonyl, aryl, substituted aryl, carbamoyl, cycloalkyl, substituted cycloalkyl, cycloalkoxycarbonyl, substituted cycloalkoxycarbonyl, heteroaryl, substituted heteroaryl, or optionally, $R^4$ and $R^5$ together with the carbon atom to which they are attached form a cycloalkyl, substituted cycloalkyl, heterocyclyl or substituted heterocyclyl ring;

each $R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;

$R^{50}$ is hydrogen, alkyl, substituted alkyl, alkenyl, substituted alkenyl, alkynyl, aryl, substituted aryl, heteroaryl or substituted heteroaryl;

$R^{61}$ is hydrogen, alkyl, substituted alkyl, alkenyl, substituted alkenyl, alkynyl, substituted alkynyl, aryl, substituted aryl, heteroaryl, substituted heteroaryl or $R^{61}$ and $R^{62}$ together with the atoms to which they are attached form a heterocyclyl ring; and $R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

BRIEF DESCRIPTION OF THE DRAWINGS

FIGS. 1-10 illustrate synthetic protocols for the synthesis of numerous compounds of this invention.

DETAILED DESCRIPTION OF THE INVENTION

This invention is directed to compounds that provide for sustained systemic concentrations of GABA analogues or active metabolites thereof following administration to animals. This invention is also directed to methods for using such compounds and pharmaceutical compositions that are used in such methods. However, prior to describing this invention in further detail, the following terms will first be defined:

DEFINITIONS

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"Administering to the animal" refers to delivering a compound of formula (I) to an animal through a suitable route. Such routes include, for example, oral, rectal, subcutaneous, intravenous, intramuscular and intranasal. Preferably, the compound is orally administered to the animal.

"Orally delivered drugs" refer to drugs which are administered to an animal in an oral form, preferably, in a pharmaceutically acceptable diluent. Oral delivery includes ingestion of the drug as well as oral gavage of the drug.

"PEPT1 oligopeptide transporter" refers to a type of protein that absorbs peptides in certain tissues, such as the intestine. This transporter is described and characterized in the literature. See Adibi, S. A., *Gastroenterology* 1997, 113, 332-340 and Leibach et al., *Ann. Rev. Nutr.* 1996, 16, 99-119 for a discussion of the transporter.

"PEPT2 oligopeptide transporter" refers to a type of protein that absorbs peptides in certain tissues, such as the kidney. This transporter is described and characterized in the literature. See Dieck, S. T. et al., *GLIA* 1999, 25, 10-20, Leibach et al., *Ann. Rev. Nutr.* 1996, 16, 99-119; and Wong et al., *Am. J. Physiol.* 1998, 275, C967-C975 for a discussion of the transporter.

"Naturally occurring amino acid" refers to any of the alpha-amino acids that are the chief components of proteins. The amino acids are either synthesized by living cells or are obtained as essential components of the diet. Such amino acids include, for example, the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"amino acid derivative" refers to a compound that contains an amino acid, or several amino acids linked by traditional peptide bonds, and that contains functional groups or substitutions on the side chain of the amino-acid or on the nitrogen atom in the pepdtide back bone.

"Systemic bioavailability" refers to the rate and extent of systemic exposure to a drug or a metabolite thereof as reflected by the area under the systemic blood concentration versus time curve.

"Translocation across the intestinal wall" refers to movement of a drug or drug conjugate by a passive or active mechanism, or both, across an epithelial cell membrane of any region of the gastrointestinal tract.

"Active metabolite of a drug" refers to products of in vivo modification of the drug that have therapeutic or prophylactic effect.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Sustained release" refers to release of a drug or an active metabolite thereof into the systemic circulation over a prolonged period of time relative to that achieved by oral administration of a conventional formulation of the drug.

"Conjugating" refers to the formation of a covalent bond.

"Active transport or active transport mechanism" refers to the movement of molecules across cellular membranes that: a) is directly or indirectly dependent on an energy mediated process (i.e. driven by ATP hydrolysis, ion gradient, etc); or b) occurs by facilitated diffusion mediated by interaction with specific transporter proteins; or c) occurs through a modulated solute channel.

"Amino-protecting group" or "amino-blocking group" refers to any group which when bound to one or more amino groups prevents reactions from occurring at these amino groups and which protecting groups can be removed by conventional chemical steps to reestablish the amino group. The particular removable blocking group is not critical and preferred amino blocking groups include, by way of example only, t-butyoxycarbonyl (t-BOC), benzyloxycarbonyl (CBZ), and the like.

"Carboxyl-protecting group" or "carboxyl-blocking group" refers to any group which when bound to one or more carboxyl groups prevents reactions from occurring at these groups and which protecting groups can be removed by conventional chemical steps to reestablish the carboxyl group. The particular removable blocking group is not critical and preferred carboxyl blocking groups include, by way of example only, esters of the formula —COOR" where R" is selected from the group consisting of alkyl, substituted alkyl, alkenyl, substituted alkenyl, aryl, substituted aryl, alkaryl, substituted alkaryl, cycloalkyl, substituted cycloalkyl, heteroaryl, substituted heteroaryl, heterocyclic, and substituted heterocyclic.

"Amino acid sidechains" refer to the sidechains of naturally occurring amino acids, which are well known in the art.

"Alkyl" refers to alkyl groups having from 1 to 20 carbon atoms and preferably 1 to 6 carbon atoms. This term is exemplified by groups such as methyl, t-butyl, n-heptyl, octyl, dodecyl and the like.

"Substituted alkyl" refers to an alkyl group having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group having from 2 to 20 carbon atoms and preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenyloxy" refers to the group —O-alkenyl.

"Substituted alkenyloxy" refers to the group —O-substituted alkenyloxy.

"Alkynyl" refers to alkynyl group having from 2 to 20 carbon atoms and preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent alkylene group having from 1 to 20 carbon atoms and preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenylene" refers to a divalent alkenylene group having from 2 to 20 carbon atoms and preferably 2 to 6 carbon atoms and having from 1 to 2 sites of alkenyl unsaturation. This term is exemplified by groups such as ethenylene (—CH═CH—), propenylene (—CH$_2$CH═CH—), and the like.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynylene" refers to a divalent alkynylene group having from 2 to 20 carbon atoms and preferably 2 to 6 carbon atoms and having from 1 to 2 sites of alkynyl unsaturation. This term is exemplified by groups such as ethynylene, propynylene and the like.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(═NH)— and the term "alkylamidino" refers to compounds having 1 to 3 alkyl groups (e.g., alkylHNC(═NH)—).

"Thioamidino" refers to the group RSC(═NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$- substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphthylene.

"Substituted arylene" refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-substituted alkenyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O—, which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 10 carbon atoms having a single cyclic ring including, by way of example, cyclopropyl, cyclobutyl, cyclopentyl, cyclohexyl, cyclooctyl and the like. This definition also includes bridged groups such as bicyclo[2.2.1]heptane and bicyclo[3.3.1]nonane.

"Cycloalkyloxy" refers to —O-cycloalkyl.

"Cycloalkenyl" refers to cyclic alkenyl groups of frm 3 to 10 carbon atoms having a single cyclic ring.

"Cycloalkenyloxy" refers to —O-cycloalkenyl.

"Substituted cycloalkyl" and "substituted cycloalkenyl" refers to an cycloalkyl or cycloalkenyl group, of from 3 to 10 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl; aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted- heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted cycloalkyloxy" and "substituted cycloalkenyloxy" refers to —O-substituted cycloalkyl and —O-substituted cycloalkenyloxy respectively.

"Cycloalkylene" refers to divalent cyclic alkylene groups of from 3 to 10 carbon atoms having a single cyclic ring including, by way of example, cyclopropylene, cyclobutylene, cyclopentylene, cyclooctylene and the like.

"Cycloalkenylene" refers to a divalent cyclic alkenylene groups of from 3 to 10 carbon atoms having a single cyclic ring.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC (=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroarylene" refers to a divalent aromatic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Amino" refers to the —$NH_2$ group.

"Substituted amino" refers to the —NR'R" group wherein R' and R" are independently hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic, substituted heterocyclic or where R' and R", together with the nitrogen atom pendent thereto, form a heterocyclic ring.

"Pharmaceutically acceptable salt" refers to pharmaceutically acceptable salts of compounds of Formulae (I)-(XIV), which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Utility

The compounds and methods described herein provide for the sustained release of the GABA analog or active metabolite thereof relative to dosing with the parent drug itself. For example, a compound and/or composition of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, ethanol withdrawal syndrome, hot flashes, gastrointestinal disorders and pathological disorders effecting the genitourinary and gastrointestinal tracts, overactive bladder, sexual dysfunction and irritable bowel syndrom. Further, in certain embodiments, the compounds and/or compositions of the invention are administered to a patient, preferably a human, as a preventative measure against various diseases or disorders. Thus, the compounds and/or compositions of the invention may be administered as a preventative measure to a patient having a predisposition for epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, ethanol withdrawal syndrome, hot flashes, gastrointestinal disorders and pathological disorders effecting the genitourinary and gastrointestinal tracts, overactive bladder, sexual dysfunction and irritable bowel syndrom. Accordingly, the compounds and/or compositions of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or compositions of the invention in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,479; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101, Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al., International Application No. WO 99/31057; Magnus-Miller et al., International Application No. WO 99/37296; Bryans et al., International Application No. WO 99/31075; Bryans et al., International Application No. WO 99/61424; Pande, International Application No. WO 00/23067; Bryans, International Application No. WO 00/31020; Bryans et al., International Application No. WO 00/50027; and Bryans et al, International Application No. WO 02/00209). Procedures for using the compounds and/or compositions of the invention for treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome have also been described in the art (see references above). Thus, it is well with the capability of those of skill in the art to assay and use the compounds and/or of the invention to treat epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome.

Preferred Embodiments

This invention facilitates sustained therapeutic or prophylactic systemic blood concentrations of GABA analogues which heretofore could not be achieved.

Accordingly, in one of its compound aspects, this invention is directed to a compound Formula (I) or (II):

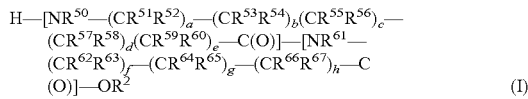

or

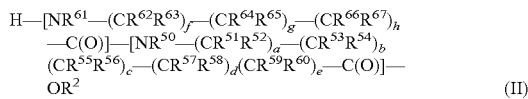

and pharmaceutically acceptable salts thereof;

wherein a, b, c, d, e, f, g and h are independently 0 or 1, provided that at least one of a, b, c, d, or e is 1; and further at least one of f, g and h is 1;

$R^2$ is hydrogen, alkyl, substituted alkyl, alkenyl, substituted alkenyl, alkynyl, aryl, substituted aryl, heteroaryl or substituted heteroaryl;

$R^{50}$ is hydrogen, alkyl, substituted alkyl, alkenyl, substituted alkenyl, alkynyl, aryl, substituted aryl, heteroaryl, substituted heteroaryl or $R^{50}$ and $R^{51}$ together with the atoms to which they are attached form a heterocyclyl ring;

$R^{51}$ is $R^{51'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring;

$R^{52}$ is $R^{52'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53}$ is $R^{53'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53}$ and $R^{54}$ together with the atoms to which they are attached form a cycloalkyl, substituted cycloalkyl, heterocyclyl or substituted heterocyclyl ring;

$R^{54}$ is $R^{54'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{55}$ is $R^{55'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{55}$ and $R^{56}$ together with the atoms to which they are attached form a cycloalkyl, substituted cycloalkyl, heterocyclyl or substituted heterocyclyl ring;

$R^{56}$ is $R^{56'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{57}$ is $R^{57'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{57}$ and $R^{58}$ together with the atoms to which they are attached form a cycloalkyl, substituted cycloalkyl, heterocyclyl or substituted heterocyclyl ring;

$R^{58}$ is $R^{58'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{59}$ is $R^{59'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{59}$ and $R^{60}$ together with the atoms to which they are attached form a cycloalkyl, substituted cycloalkyl, heterocyclyl or substituted heterocyclyl ring;

$R^{60}$ is $R^{60'}$, hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{61}$ is hydrogen, alkyl, substituted alkyl, alkenyl, substituted alkenyl, alkynyl, substituted alkynyl, aryl, substituted aryl, heteroaryl, substituted heteroaryl or $R^{61}$ and $R^{62}$ together with the atoms to which they are attached form a heterocyclyl ring;

$R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{62}$ and $R^{63}$ together with the atoms to which they are attached form a cycloalkyl, substituted cycloalkyl, heterocyclyl or substituted heterocyclyl ring;

$R^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{64}$ and $R^{65}$ together with the atoms to which they are attached form a cycloalkyl, substituted cycloalkyl, heterocyclyl or substituted heterocyclyl ring;

$R^{65}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{66}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{66}$ and $R^{67}$ together with the atoms to which they are attached form a cycloalkyl, substituted cycloalkyl, heterocyclyl or substituted heterocyclyl ring;

$R^{67}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

and wherein each of $R^{51'}$ through $R^{60'}$ is independently selected from the group consisting of alkylene-D, substituted alkylene-D, alkenylene-D, substituted alkenylene-D, alkynylene-D, substituted alkynylene-D, cycloalkylene-D, substituted cycloalkylene-D, heterocyclylene-D, substituted heterocyclylene-D, arylene-D, substituted arylene-D, heteroarylene-D and substituted heteroarylene-D, wherein D is selected from the group consisting of:

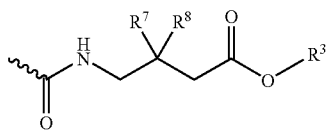
i

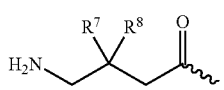
ii

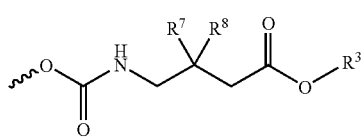
iii

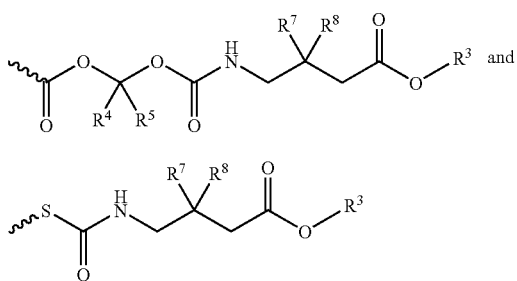
iv
and
v wherein $R^3$ is hydrogen, alkyl, substituted alkyl, alkenyl, substituted alkenyl, alkynyl, aryl, substituted aryl, heteroaryl and substituted heteroaryl;

each $R^4$ and $R^5$ are independently selected from the group consisting of hydrogen, alkyl, substituted alkyl, alkoxycarbonyl, substituted alkoxycarbonyl, aryl, substituted aryl, carbamoyl, cycloalkyl, substituted cycloalkyl, cycloalkoxycarbonyl, substituted cycloalkoxycarbonyl, heteroaryl, substituted heteroaryl, or optionally, $R^4$ and $R^5$ together with the carbon atom to which they are attached form a cycloalkyl, substituted cycloalkyl, heterocyclyl or substituted heterocyclyl ring;

each $R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;

provided that at least one of $R^{51}$ through $R^{60}$ is $R^{51'}$ through $R^{60'}$.

In a preferred embodiment of this invention, a, b, c, d, e, f, g and h are selected to provide a dipeptide composed of two α-amino acids, i.e., a=1; b, c, d and e=0; f=1, and g and h=0. Particularly preferred compounds can be represented by Formulae (III) and (IV):

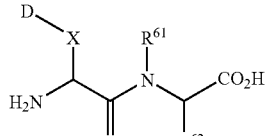
(III)

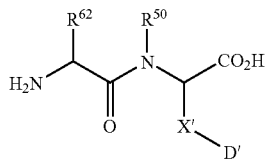
(IV)

and pharmaceutically acceptable salts thereof;

where X and X' are independently selected from the group consisting of alkylene, substituted alkylene, alkenylene, substituted alkenylene, alkynylene, substituted alkynylene, cycloalkylene, substituted cycloalkylene, heterocyclylene, substituted heterocyclylene, arylene, substituted arylene, heteroarylene and substituted heteroarylene;

D and D' are independently selected from the group consisting of:

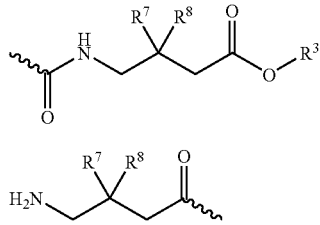
i ii

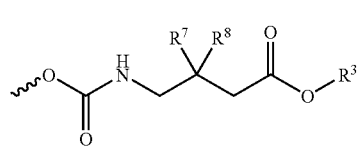
iii

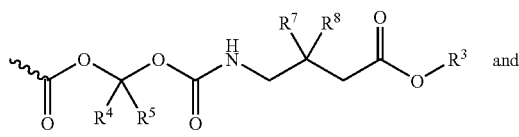
iv
and
v

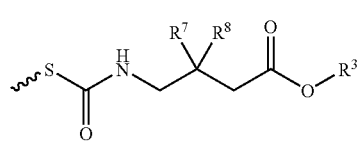

wherein $R^3$ is hydrogen, alkyl, substituted alkyl, alkenyl, substituted alkenyl, alkynyl, aryl, substituted aryl, heteroaryl and substituted heteroaryl;

each $R^4$ and $R^5$ are independently selected from the group consisting of hydrogen, alkyl, substituted alkyl, alkoxycarbonyl, substituted alkoxycarbonyl, aryl, substituted aryl, carbamoyl, cycloalkyl, substituted cycloalkyl, cycloalkoxycarbonyl, substituted cycloalkoxycarbonyl, heteroaryl, substituted heteroaryl, or optionally, $R^4$ and $R^5$ together with the carbon atom to which they are attached form a cycloalkyl, substituted cycloalkyl, heterocyclyl or substituted heterocyclyl ring;

each $R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;

$R^{50}$ is hydrogen, alkyl, substituted alkyl, alkenyl, substituted alkenyl, alkynyl, aryl, substituted aryl, heteroaryl or substituted heteroaryl;

$R^{61}$ is hydrogen, alkyl, substituted alkyl, alkenyl, substituted alkenyl, alkynyl, substituted alkynyl, aryl, substituted aryl, heteroaryl, substituted heteroaryl or $R^{61}$ and $R^{62}$ together with the atoms to which they are attached form a heterocyclyl ring; and $R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

Preferably, in this embodiment each amino acid is an L-amino acid and more preferably, each amino acid is a naturally occurring amino acid.

In still another preferred embodiment of compounds of Formula (III) and (IV), $R^7$ and $R^8$ are independently selected from the group consisting of hydrogen, alkyl, substituted alkyl, cycloalkyl, substituted cycloalkyl, heterocyclyl and substituted heterocyclyl. Preferably, $R^7$ and $R^8$ are independently selected from the group consisting of hydrogen, alkyl and substituted alkyl. In another embodiment, $R^7$ and $R^8$ together with the carbon atom to which they are attached form a cycloalkyl or substituted cycloalkyl ring. Preferably, $R^7$ and $R^8$ together with the carbon atom to which they are attached form a cyclobutyl, substituted cyclobutyl, cyclopentyl, substituted cyclopentyl, cyclohexyl or substituted cyclohexyl ring. In another embodiment, $R^7$ and $R^8$ together with the carbon atom to which they are attached form a heterocyclyl or substituted heterocyclyl ring.

Preferred compounds of the invention include compounds of Formulae (V)-(XIV):

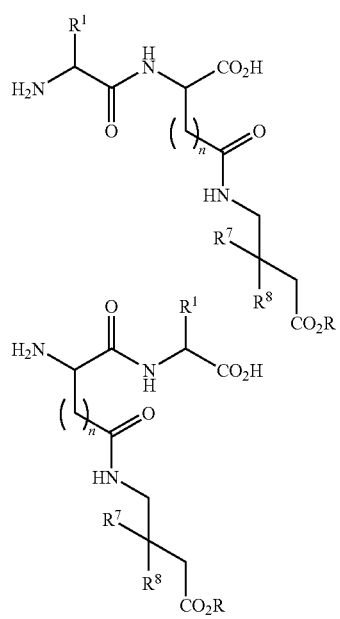

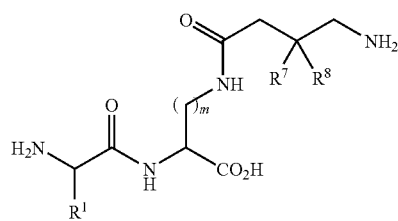

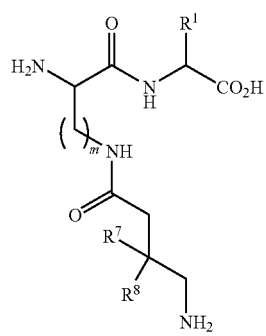

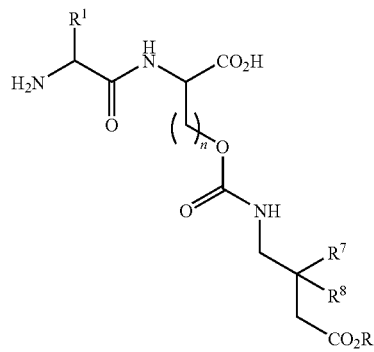

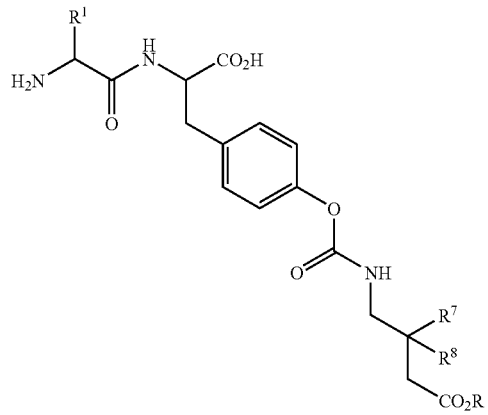

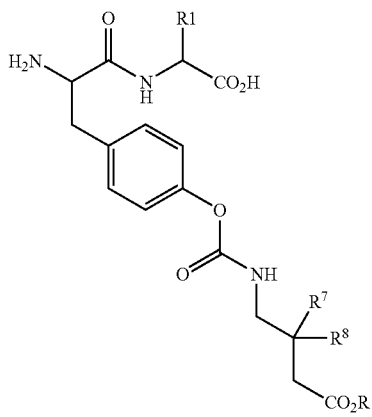

(XI)

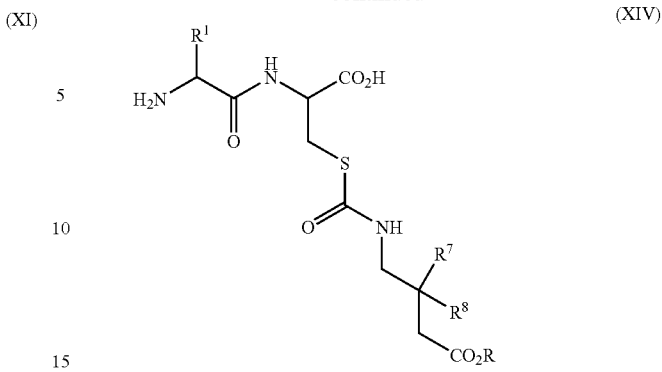

(XII)

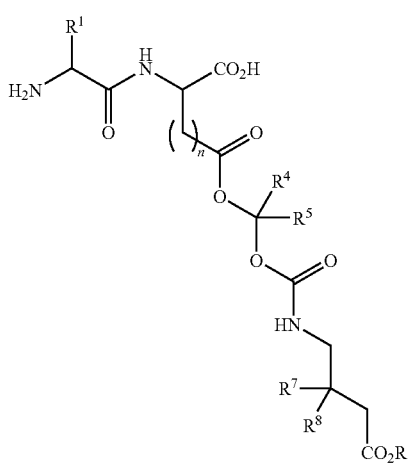

(XIV)

wherein n is 1 or 2;
m is 1, 2, 3 or 4;

$R^1$ is selected from the group consisting of hydrogen, methyl, isopropyl, isobutyl, sec-butyl, —$CH_2OH$, —CH(OH)$CH_3$, —$CH_2CO_2H$, —$CH_2CH_2CO_2H$, —$CH_2CONH_2$, —$CH_2CH_2CONH_2$, —$CH_2CH_2SCH_3$, $CH_2SH$, —$CH_2(CH_2)_3NH_2$ or —$CH_2CH_2CH_2NHC(NH)NH_2$, phenyl, benzyl, 4-hydroxybenzyl, 2-imidazolyl and 2-indolyl;

R is selected from the group consisting of hydrogen, $C_{1-6}$ alkyl, phenyl, benzyl, —C($CH_3$)=$CH_2$ or —$CH_2C(O)N(CH_3)_2$;

either $R^4$ is hydrogen and $R^5$ is selected from the group consisting of methyl, ethyl, propel, isopropyl, butyl, isobutyl, sec-butyl, tert-butyl, cyclopentyl, cyclohexyl, phenyl, benzyl, phenethyl or 3-pyridyl; or $R^4$ is methyl and $R^5$ is selected from the group consisting of methyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and cyclohexyloxycarbonyl;

either $R^7$ and $R^8$ together with the atom to which they are attached form a cyclohexyl ring, or $R^7$ is hydrogen and $R^8$ is isobutyl; and pharmaceutically acceptable salts thereof.

In a method aspect of this invention, the compounds of this invention are preferably used in a method for achieving sustained therapeutic or prophylactic blood concentrations of a GABA analog or an active metabolite thereof in the systemic circulation of an animal. The method involves administering a compound of formula (I) to an animal.

In a composition aspect of this invention, the compounds of this invention are mixed with a pharmaceutically acceptable carrier to provide a composition. The composition is preferably used in the method of achieving sustained therapeutic or prophylactic blood concentrations of a GABA analog or an active metabolite thereof discussed above.

Compound Preparation

Compounds of the invention are dipeptides comprised of an α-, β- or γ-amino acid linked to either an α-, β-, γ-, δ- or ε-amino acid, wherein a GABA analog is chemically conjugated via a side chain of one of the two constituent amino acids. Compounds of the invention can be made by various methods, including those illustrated in FIGS. 1-10 and the working examples provided below. Gabapentin (1) serves as a representative GABA analog for illustrative purposes in these figures and examples, and the skilled artisan will appreciate that these synthetic methods are in no way limited to the particular choice of GABA analog. Similarly, the choice of α-amino acids as constituents of the dipeptides to which the GABA analog is ultimately conjugated in these examples is also purely illustrative. In compounds of the invention where

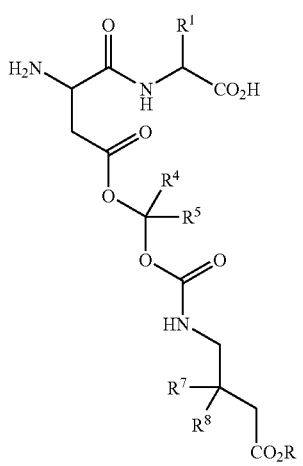

(XIII)

the GABA analog is conjugated via its terminal amino moiety to the dipeptide, its carboxyl moiety is present either as a free carboxylic acid or as a carboxylic ester. Formation of such carboxylic esters is typically performed after conjugation of the amino moiety of the GABA analog, and any of the well-known methods of carboxyl group esterification (e.g. condensation with an alcohol, alkylation of a carboxylate anion with an alkyl halide, reaction of a carboxylic acid with a diazoalkane) may be utilized. The carboxyl group methylation in FIGS. 1, 2, 5-10 is again illustrative.

FIGS. 1 and 2 describe the preparation of gabapentin derivatives (17)-(20) and (32)-(35) conjugated to dipeptides via the side chain of aspartic or glutamic acid through amide linkages. FIGS. 3 and 4 describe the preparation of gabapentin derivatives (53)-(56) and (73)-(76) conjugated to dipeptides via the side chain of diaminopropionic acid, diaminobutyric acid, ornithine or lysine through amide linkages. FIG. 5 describes the preparation of gabapentin derivatives (86)-(89) conjugated to dipeptides via the side chain of serine or homoserine through carbamate linkages. FIGS. 6 and 7 describe the preparation of gabapentin derivatives (94), (95), (100) and (101) conjugated to dipeptides via the side chain of tyrosine through carbamate linkages. FIGS. 8 and 9 describe the preparation of gabapentin derivatives (113)-(116), (120) and (121) conjugated to dipeptides via the side chain of aspartic or glutamic acid through acyloxyalkylcarbamate linkages. FIG. 10 describes the preparation of gabapentin derivatives (127) and (128) conjugated to dipeptides via the side chain of cysteine through thiocarbamate linkages.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1-15 (John Wiley and Sons, 1991); Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Pharmaceutical Formulations

When employed as pharmaceuticals, the compounds of Formula (I)-(XIV) are usually administered in the form of pharmaceutical compositions. These compounds can be administered by a variety of routes including oral, rectal, subcutaneous, intravenous, intramuscular and intranasal. These compounds are effective as both injectable and oral compositions. Compositions for oral administration are particularly preferred. Such compositions are prepared in a manner well known in the pharmaceutical art and comprise at least one active compound.

This invention also includes pharmaceutical compositions which contain, as the active ingredient, one or more of the compounds of Formula (I)-(XIV) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art. Compositions that provide for sustained release of the active ingredient are particularly preferred.

The compositions are preferably formulated in a unit dosage form, each dosage containing from about 0.1 to about 5000 mg, more usually about 10 to about 2000 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. Osmotic delivery systems are also useful for oral sustained release administration (Verma et al., *Drug Dev. Ind. Pharm.*, 2000, 26:695-708). In a preferred embodiment, OROS™ osmotic devices are used for oral sustained release delivery devices (Theeuwes et al., U.S. Pat. No. 3,845,770; Theeuwes et al., U.S. Pat. No. 3,916,899).

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

Example 1

Synthesis of N-β-(Gabapentinyl)-L-Diaminopropionyl-Gabapentin

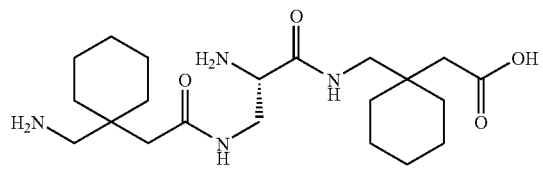

N-Boc-Gabapentin

Gabapentin hydrochloride (5 g, 24 mmol), (Boc)$_2$O (6.3 g, 29 mmol), NaOH (3 g, 72 mmol) and water (50 mL) was stirred at ambient temperature for 16 h. The reaction was acidified to pH 3 with citric acid and extracted with diethyl ether (100 mL). The organic layer was separated and washed with 0.5 M aqueous citric acid (100 mL) and water (2×100 mL). The organic phase was separated, dried over MgSO$_4$, filtered and concentrated under reduced pressure to afford N-Boc-Gabapentin (6 g, 22 mmol, 92%) as a white solid.

N-α-Boc-N-β-(N-Boc-Gabapentin)-L-Diaminopropionic Acid

A solution of N-Boc-Gabapentin (6 g, 22 mmol), N-hydroxysuccinmaide (3.09 g, 26.4 mmol) and dicyclohexylcarbodiimide (5.44 g, 26.4 mmol) in acetonitrile (100 mL) was stirred at ambient temperature for 16 h. The reaction was filtered and the solvent was evaporated under reduced pressure leaving a white foam. The foam was dissolved in N,N-dimethylacetamide (40 mL) and added to a solution of N-α-Boc-L-diamino-propionic acid (10 g, 49 mmol) and NaOH (1.86 g, 47 mmol) in water (40 mL). The reaction was stirred at ambient temperature for 16 h. The reaction was diluted with 0.5 M aqueous citric acid (500 mL) and extracted with diethyl ether (250 mL). The organic phase was separated and washed with 0.5 M aqueous citric acid (250 mL) and water (2×250 mL). The organic phase was separated, dried over MgSO$_4$, filtered, and concentrated under reduced pressure to afford N-α-Boc-N-β-(N-Boc-gabapentin)-L-diaminopropionic acid (10.2 g, 22 mmol) as a white foam.

N-β-(Gabapentinyl)-L-Diaminopropionyl-Gabapentin

A solution of N-α-Boc-N-β-(N-Boc-gabapentin)-L-diaminopropionic acid (457 mg, 1 mmol), N-hydroxysuccinamide (138 mg, 1.2 mmol) and dicyclohexylcarbodiimide (247 mg, 1.2 mmol) in acetonitrile (10 mL) was shaken at ambient temperature for 24 h. The reaction was filtered and the solvent was evaporated under reduced pressure leaving a colorless syrup. The syrup was dissolved in N,N-dimethylacetamide (2 mL) and added to a solution of gabapentin hydrochloride (415 mg, 2 mmol) and NaOH (156 mg, 3.9 mmol) in water (4 mL). The reaction was shaken at ambient temperature for 24 h. The reaction was diluted with diethyl ether (100 mL) and washed with 0.5 M aqueous citric acid (2×100 mL) and water (2×100 mL). The organic phase was separated, dried over MgSO$_4$, filtered, and concentrated under reduced pressure to afford N-α-Boc-N-β-(N-Boc-gabapentin)-L-diaminopropionyl-gabapentin as a white foam. The foam was dissolved in trifluoroacetic acid (40 mL) and allowed to stand at ambient temperature for 30 minutes. The solvent was removed under reduced pressure. The residue was dissolved in water (4 mL) and filtered through a 0.25 μm nylon membrane filter prior to purification by preparative HPLC (Phenomenex LUNA C$_{18}$, 250×21.2 mm, 5 μm column, eluting with 100% water for 5 min., then 0-60% acetonitrile in water with 0.05% TFA over 20 min. at 20 mL/min). The pure fractions were combined and the solvent was removed under reduced pressure to afford N-β-(gabapentinyl)-L-diaminopropionyl-gabapentin (107 mg) as a white solid. $^1$H NMR (CD$_3$OD, 400 MHz): 1.2-1.6 (m, 20H), 2.3 (s, 2H), 2.45 (s, 2H), 3.0 (s, 2H), 3.35 (m, 2H), 3.63 (d, 2H), 4.07 (t, 1H). MS (ESI) m/z 409.40 (M−H$^-$), 411.41 (M+H$^+$).

Example 2

Synthesis of N-β-(Gabapentinyl)-L-Diaminopropionyl-L-Alanine

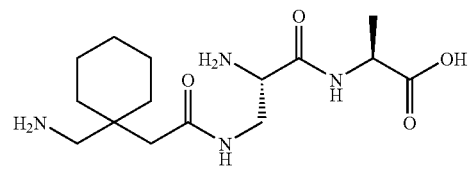

A solution of N-α-Boc-N-β-(N-Boc-gabapentin)-L-diaminopropionic acid (0.75 g, 1.64 mmol) and O-(7-azabenzotriazol-1-yl)-N,N,N',N'-tetramethyluronium hexafluorophosphate (HATU), (0.8 g, 2.1 mmol) in N,N-dimethylacetamide (DMA), (4 mL) was stirred at room temperature for 1 h. The resulting solution was added to a suspension of H-Ala-2-Cl Trityl resin (0.250 g, 0.5 mmol/g) in DMA (2 mL) followed by diisopropylethylamine (0.66 mL, 3.7 mmol) and shaken overnight at room temperature. The reaction mixture was filtered, and the resin was washed successively with DMF, THF and CH$_2$Cl$_2$. After drying under vacuum, the resin was treated with TFA (4mL) at room temperature for 5 h. The reaction mixture was filtered and the resin was washed with CH$_2$Cl$_2$ (2×2 mL). The combined filtrate was evaporated under reduced pressure. The product was purified by preparative HPLC (using conditions described above) to afford pure N-β-(gabapentinyl)-L-diaminopropionyl-L-alanine as a white solid (10 mg, 30% yield). $^1$H NMR (CD$_3$OD, 400 MHz): 1.35-1.62 (m, 13H), 2.45 (s, 2H), 2.97 (s, 2H), 3.64 (m, 2H), 4.23 (m, 1H), 4.61 (m, 1H). MS (ESI) m/z 327.41 (M−H$^−$), 329.26 (M+H$^+$).

Example 3

Synthesis of N-β-(Gabapentinyl)-L-Diaminopropionyl-L-Aspartic Acid

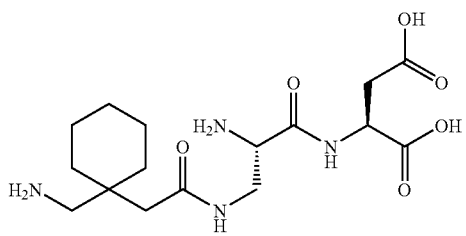

A solution of N-α-Boc-N-β-(N-Boc-gabapentin)-L-diaminopropionic acid (0.75 g, 1.64 mmol) and O-(7-azabenzotriazol-1-yl)-N,N,N',N'-tetramethyluronium hexafluorophosphate (HATU), (0.8 g, 2.1 mmol) in N,N-dimethylacetamide (DMA), (4 mL) was stirred at room temperature for 1 h. The resulting solution was added to a suspension of H-Asp-(O-tert-Butyl)-2-Cl Trityl resin (0.250 g, 0.5 mmol/g) in DMA (2 mL) followed by diisopropylethylamine (0.66 mL, 3.7 mmol) and shaken overnight at room temperature. The reaction mixture was filtered, and the resin was washed successively with DMF, THF and CH$_2$Cl$_2$. After drying under vacuum, the resin was treated with TFA (4 mL) at room temperature for 5 h. The reaction mixture was filtered and the resin was washed with CH$_2$Cl$_2$ (2×2 mL). The combined filtrate was evaporated under reduced pressure. The product was purified by preparative HPLC (using conditions described above) to afford pure N-β-(gabapentinyl)-L-diaminopropionyl-L-aspartic acid as a white solid (3 mg). $^1$H NMR (CD$_3$OD, 400 MHz): 1.35-1.65 (m, 10H), 2.47 (s, 2H), 2.74 (s, 2H), 2.99 (s, 2H), 3.70 (m, 2H), 4.55 (m, 1H), 4.90 (m, 1H). MS (ESI) m/z 371.37 (M−H$^−$), 373.29 (M+H$^+$).

Example 4

Synthesis of N-β-(Gabapentinyl)-L-Diaminopropionyl-L-Serine

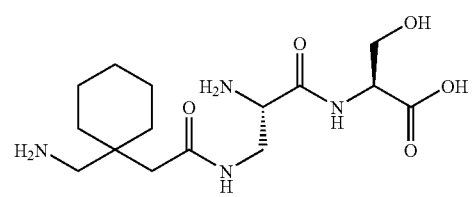

A solution of N-α-Boc-N-β-(N-Boc-gabapentin)-L-diaminopropionic acid (0.75 g, 1.64 mmol) and O-(7-azabenzotriazol-1-yl)-N,N,N',N'-tetramethyluronium hexafluorophosphate (HATU), (0.8 g, 2.1 mmol) in N,N-dimethylacetamide (DMA), (4 mL) was stirred at room temperature for 1 h. The resulting solution was added to a suspension of H-Ser-(O-tert-Butyl)-2-Cl Trityl resin (0.250 g, 1.7 mmol/g) in DMA (2 mL) followed by diisopropylethylamine (0.66 mL, 3.7 mmol) and shaken overnight at room temperature. The reaction mixture was filtered, and the resin was washed successively with DMF, THF and CH$_2$Cl$_2$. After drying under vacuum, the resin was treated with TFA (4mL) at room temperature for 5 h. The reaction mixture was filtered and the resin was washed with CH$_2$Cl$_2$ (2×2 mL). The combined filtrate was evaporated under reduced pressure. The product was purified by preparative HPLC (using conditions described above) to afford pure N-β-(gabapentinyl)-L-diaminopropionyl-L-serine as a white solid (20 mg, 36% yield). $^1$H NMR (CD$_3$OD, 400 MHz): 1.30-1.63 (m, 10H), 2.51 (s, 2H), 3.05 (s, 2H), 3.70 (m, 2H), 3.91 (m, 2H), 4.12 (m, 1H), 4.49 (m, 1H). MS (ESI) m/z 343.34 (M−H$^−$), 345.23 (M+H$^+$).

Example 5

In Vitro Compound Transport Assays with PEPT1 and PEPT2-Expressing Cell Lines (a) Inhibition of Radiolabeled Gly-Sar Uptake Rat and human PEPT1 and PEPT2 expressing CHO cell lines were prepared as described in PCT Application WO01/20331. Gabapentin-containing dipeptides were evaluated for interaction with the peptide transporters using a radiolabeled substrate uptake assay in a competitive inhibition format, as described in PCT Application WO01/20331. Transport-induced currents were also measured in *Xenopus* oocytes transfected with rat and human PEPT1 and PEPT2.

(b) Analysis of Electrogenic Transport in *Xenopus* Oocytes

RNA Preparation:

Rat and human PEPT1 and PEPT2 transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

41

*Xenopus* Oocyte Isolation.

*Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 min with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10-20 µg RNA in 45 µL solution.

Electrophysiology Measurements.

Transport currents were measured 2-14 days after injection, using a standard two-electrode electrophysiology set-up (Geneclamp 500 amplifier, Digidata 1320/PCLAMP software and ADInstruments hardware and software were used for signal acquisition). Electrodes (2-4 mΩ) were microfabricated using a Sutter Instrument puller and filled with 3M KCl. The bath was directly grounded (transporter currents were less than 0.3 µA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4-8 Hz. All bath and drug-containing solutions were frog ringers solution containing $CaCl_2$. Drugs were applied for 10-30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to transport rate. Recordings were made from a single oocyte for up to 60 min, enabling 30-40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycyl-sarcosine (1 mM) was used as a common reference to normalize results from test compounds. Using this normalization procedure $I_{max}$ (i.e. maximal induced current) for different compounds tested on different oocytes could be compared. N-β-(gabapentinyl)-L-diaminopropionyl-L-alanine elicited 45% of $I_{max}$ on PEPT2-expressing oocytes when tested at a concentration of 1 mM, indicating that this compound was an effective substrate for this transporter.

In view of the above disclosure, it is understood, of course, that combinations of substituents within the compounds of the present invention do not include any combination that is chemically impossible or non-feasible as would be appreciated by one skilled in the art.

42

What is claimed is:

1. A compound of Formulae (V)-(XIV):

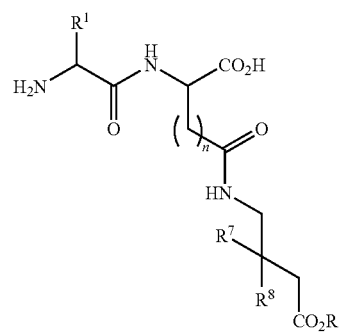

(V)

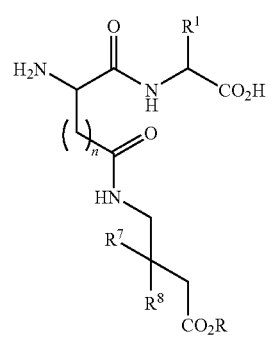

(VI)

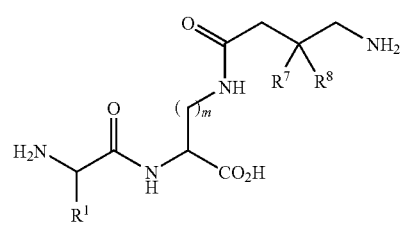

(VII)

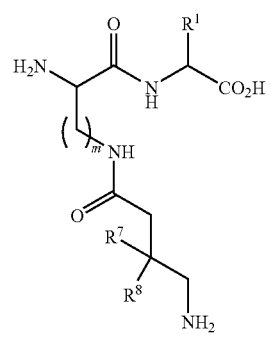

(VIII)

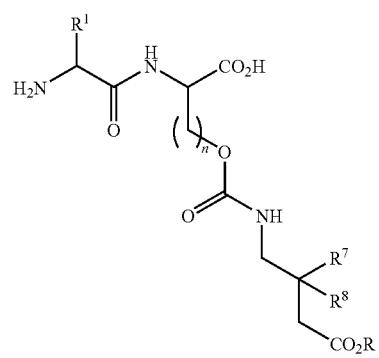

(IX)

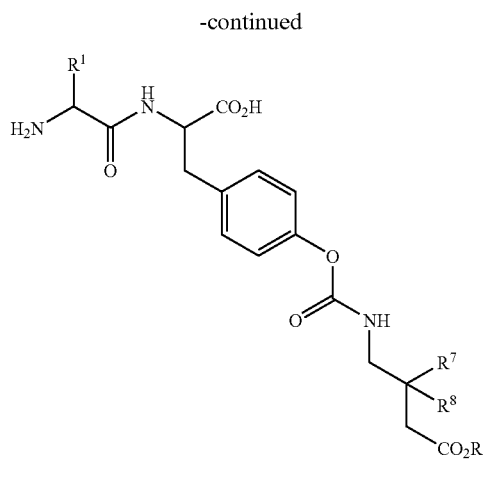
(X)

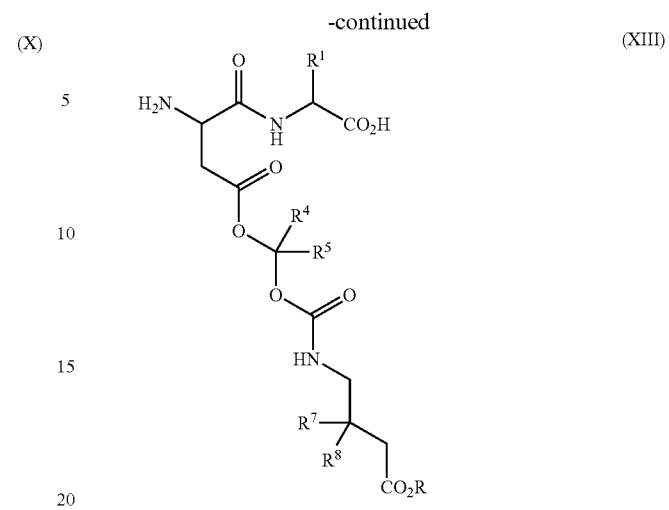
(XIII)

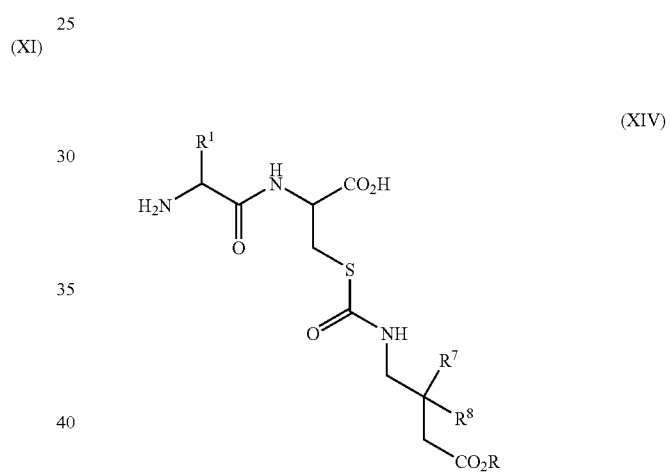
(XIV)

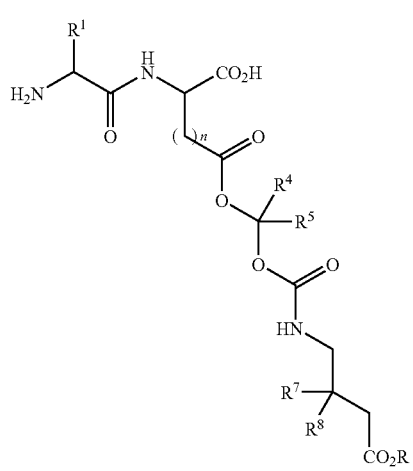
(XI)

(XII)

wherein n is 1 or 2;

m is 1, 2, 3 or 4;

$R^1$ is selected from the group consisting of hydrogen, methyl, isopropyl, isobutyl, sec-butyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, $CH_2SH$, —$CH_2(CH_2)_3NH_2$ or —$CH_2CH_2CH_2NHC(NH)NH_2$, phenyl, benzyl, 4-hydroxybenzyl, 2-imidazolyl and 2-indolyl;

R is selected from the group consisting of hydrogen, $C_{1-6}$ alkyl, phenyl, benzyl, —$C(CH_3)$=$CH_2$ or —$CH_2C(O)N(CH_3)_2$;

either $R^4$ is hydrogen and $R^5$ is selected from the group consisting of methyl, ethyl, propyl, isopropyl, butyl, isobutyl, sec-butyl, tert-butyl, cyclopentyl, cyclohexyl, phenyl, benzyl, phenethyl or 3-pyridyl; or $R^4$ is methyl and $R^5$ is selected from the group consisting of methyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and cyclohexyloxycarbonyl;

$R^7$ is hydrogen;

$R^8$ is substituted aryl; and pharmaceutically acceptable salts thereof.

2. The compound of claim 1, wherein the compounds of Formula V and Formula VI are each L-amino acids or L-amino acid derivatives.

3. The compound of claim 2, wherein $R^8$ is para-chloro-substituted phenyl.

4. A pharmaceutical composition comprising a pharmaceutically acceptable carrier and an effective amount of a compound or mixture of compounds according to claim 1.

* * * * *